United States Patent
Tsushima et al.

(10) Patent No.: US 11,918,668 B2
(45) Date of Patent: Mar. 5, 2024

(54) METHOD FOR PRODUCING GLYCERYL ETHER-CONTAINING COMPOSITION, AND GLYCERYL ETHER-CONTAINING COMPOSITION

(71) Applicant: ADEKA CORPORATION, Tokyo (JP)

(72) Inventors: Yasuhiro Tsushima, Tokyo (JP); Hiroshi Suzuki, Tokyo (JP); Kazuya Nakajima, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 87 days.

(21) Appl. No.: 17/277,924

(22) PCT Filed: Sep. 20, 2019

(86) PCT No.: PCT/JP2019/036970
§ 371 (c)(1),
(2) Date: Mar. 19, 2021

(87) PCT Pub. No.: WO2020/066893
PCT Pub. Date: Apr. 2, 2020

(65) Prior Publication Data
US 2021/0353515 A1 Nov. 18, 2021

(30) Foreign Application Priority Data
Sep. 25, 2018 (JP) ................. 2018-178640

(51) Int. Cl.
*A61K 8/33* (2006.01)
*A61K 8/67* (2006.01)

(52) U.S. Cl.
CPC .............. *A61K 8/33* (2013.01); *A61K 8/67* (2013.01); *A61K 2800/10* (2013.01); *A61K 2800/522* (2013.01); *A61K 2800/805* (2013.01)

(58) Field of Classification Search
None
See application file for complete search history.

(56) References Cited

U.S. PATENT DOCUMENTS

| | | | | |
|---|---|---|---|---|
| 2,140,794 A | * | 12/1938 | Epstein | .............. C11B 3/001 554/205 |
| 2002/0142019 A1 | * | 10/2002 | Kuhnau | ............. A61K 8/676 514/474 |
| 2003/0149097 A1 | | 8/2003 | Beilfuss et al. | |
| 2006/0046943 A1 | | 3/2006 | Erazo-Majewicz et al. | |
| 2010/0310487 A1 | | 12/2010 | Beilfuss et al. | |
| 2016/0227827 A1 | * | 8/2016 | Grass | .................. A23L 2/58 |

FOREIGN PATENT DOCUMENTS

| | | |
|---|---|---|
| EP | 2 316 410 | 5/2011 |
| JP | 6-80600 | 3/1994 |
| JP | 10-46024 | 2/1998 |
| JP | 2003-138087 | 5/2003 |
| JP | 2005-170878 | 6/2005 |
| JP | 2007-016018 | 1/2007 |
| JP | 2007-161651 | 6/2007 |
| JP | 2007-297320 | 11/2007 |
| JP | 201157647 | * 3/2011 |
| WO | 2015/125392 | 8/2015 |

OTHER PUBLICATIONS

Written Opinion of the International Searching Authority, PCT/JP2019/036970, dated Nov. 26, 2019 (Year: 2019).*
Machine Translation of JP H10-46024, obtained from IP.com, Feb. 17, 1998 (Year: 1998).*
International Search Report dated Nov. 26, 2019 in International (PCT) Application No. PCT/JP2019/036970.
Extended European Search Report dated Jun. 3, 2022, in corresponding European Patent Application No. 19867021.8.

* cited by examiner

*Primary Examiner* — Jennifer A Berrios
(74) *Attorney, Agent, or Firm* — Wenderoth, Lind & Ponack, L.L.P.

(57) ABSTRACT

The present invention provides a method for producing a glyceryl ether-containing composition, the method including: a deodorization step for bringing a glyceryl ether-containing product selected from the group consisting of a monohexyl glyceryl ether-containing product, a monocyclohexyl glyceryl ether-containing product and a mixture thereof into contact with water vapor in an environment having a reduced pressure of 0.10 kPa or more and 10 kPa or less for 60 minutes or more and 600 minutes or less; and an addition step for adding 0.05 to 0.30 parts by mass of an antioxidant containing d-α-tocopherol to 100 parts by mass of the glyceryl ether-containing product, and also provides a glyceryl ether-containing composition containing specific amounts of a specific glyceryl ether and an antioxidant containing d-α-tocopherol.

2 Claims, No Drawings

METHOD FOR PRODUCING GLYCERYL ETHER-CONTAINING COMPOSITION, AND GLYCERYL ETHER-CONTAINING COMPOSITION

TECHNICAL FIELD

The present invention relates to a method for producing a glyceryl ether-containing composition, with which it is possible to adequately prevent oxidative degradation, decomposition over time and generation of unpleasant odors during storage while still maintaining quality over a long period of time, and also relates to a glyceryl ether-containing composition.

BACKGROUND ART

Antimicrobial agents are commonly used for purposes such as preservation in cosmetics, detergents, and the like. Parabens are most commonly used as the antimicrobial agents. However, parabens have the drawback of being limited in terms of concentration for usage due to causing high skin irritation and low safety, and are limited in terms of concentration for usage to 1 mass % or less in cosmetics. In addition, in recent years the number of people showing allergic reactions to parabens has increased, and demands for paraben-free cosmetics are increasing.

As a result, use is known of diol compounds, such as alkane diols and alkyl glyceryl ether compounds, and compounds obtained by adding alkylene oxides to these diol compounds, as antimicrobial agents (for example, see Patent Documents 1 to 3). These compounds have the characteristics of exhibiting greater safety to humans than parabens while exhibiting favorable performance as antimicrobial agents, and the use of these compounds as preservatives in cosmetics instead of parabens is increasing.

CITATION LIST

Patent Literature

[Patent Document 1] Japanese Patent Application Laid Open No. 2005-170878
[Patent Document 2] Japanese Patent Application Laid Open No. 2007-016018
[Patent Document 3] Japanese Patent Application Laid Open No. 2007-161651

SUMMARY OF INVENTION

Technical Problem

Among the diol compounds mentioned above, hexyl glyceryl ether and cyclohexyl glyceryl ether are known to exhibit high antimicrobial activity due to their chemical structures. However, it has been found that, for example, when stored for a long period of time in a high temperature environment, these glyceryl ethers undergo oxidative degradation and decomposition over time particularly readily due to having relatively low molecular weights, and suffer from long term quality stability problems such as an increase in the amount of low molecular weight components that are a source of odors. The oxidative degradation and decomposition over time are particularly prominent for hexyl glyceryl ether and cyclohexyl glyceryl ether, and it has been impossible to adequately prevent oxidative degradation and decomposition over time during storage of cosmetics and the like that contain hexyl glyceryl ether-containing compositions and cyclohexyl glyceryl ether-containing compositions. Therefore, the problem to be solved by the present invention is to provide a method for producing a glyceryl ether-containing composition, with which it is possible to adequately prevent oxidative degradation, decomposition over time and generation of unpleasant odors during storage and maintain quality over a long period of time, and also provide a glyceryl ether-containing composition.

Solution to Problem

The inventors of the present invention completed the present invention as a result of diligent research. That is, the present invention is a method for producing a glyceryl ether-containing composition, the method comprising: a deodorization step for bringing a glyceryl ether-containing product selected from the group consisting of a monohexyl glyceryl ether-containing product, a monocyclohexyl glyceryl ether-containing product and a mixture thereof into contact with water vapor in an environment having a reduced pressure of 0.10 kPa or more and 10 kPa or less for 60 minutes or more and 600 minutes or less; and an addition step for adding 0.05 to 0.30 parts by mass of an antioxidant containing d-α-tocopherol to 100 parts by mass of the glyceryl ether-containing product.

Advantageous Effects of Invention

According to the present invention, it is possible to provide a method for producing a glyceryl ether-containing composition, with which it is possible to adequately prevent oxidative degradation, decomposition over time and generation of unpleasant odors during storage and maintain quality over a long period of time, and also provide a glyceryl ether-containing composition.

DESCRIPTION OF EMBODIMENTS

The method for producing a glyceryl ether-containing composition of the present invention comprises: a deodorization step for bringing a glyceryl ether-containing product selected from the group consisting of a monohexyl glyceryl ether-containing product, a monocyclohexyl glyceryl ether-containing product and a mixture thereof into contact with water vapor in an environment having a reduced pressure of 0.10 kPa or more and 10 kPa or less for 60 minutes or more and 600 minutes or less; and an addition step for adding 0.05 to 0.30 parts by mass of an antioxidant containing d-α-tocopherol to 100 parts by mass of the glyceryl ether-containing product. In the method for producing the glyceryl ether-containing composition of the present invention, these deodorization and addition steps are essential in order to maintain quality over a long period of time.

The method for producing the monohexyl glyceryl ether-containing product and monocyclohexyl glyceryl ether-containing product used in the present invention may be any well-known method, examples of which include a method comprising subjecting hexanol and glycerin to a dehydrating condensation reaction, a method comprising subjecting hexyl chloride or hexyl bromide and glycerin to a dehydrochlorination reaction, a method comprising subjecting hexanol and 1-chloro-2,3-propane diol to a dehydrochlorination reaction, a method comprising reacting hexanol with epichlorohydrin and then hydrolyzing the obtained hexyl glycidyl ether, a method comprising reacting hexanol with glycidol, and a method comprising subjecting hexanol and allyl chloride to a dehydrochlorination reaction, then oxidizing with hydrogen peroxide or the like, and hydrolyzing the obtained hexyl glycidyl ether. In addition, products having high purity can be obtained if reactions in which glycerin is used are carried out using a method comprising carrying out the reactions mentioned above using a product obtained by partially esterifying glycerin with a lower fatty acid and, following completion of the reaction, removing the fatty acid by saponification or using a method comprising carrying out the reactions mentioned above using a partially ketalated product of glycerin and, following completion of the reaction, decoupling the ketal.

Of these methods, a method comprising reacting hexanol with epichlorohydrin and then hydrolyzing the obtained hexyl glycidyl ether is preferred as the method for producing a monohexyl glyceryl ether-containing product from the perspective of being able to produce the product inexpensively on an industrial scale. For similar reasons, a method comprising reacting cyclohexanol with epichlorohydrin and then hydrolyzing the obtained cyclohexyl glycidyl ether is preferred as the method for producing a monocyclohexyl glyceryl ether-containing product.

Moreover, monohexyl glyceryl ether-containing products and monocyclohexyl glyceryl ether-containing products produced using methods such as those described above can, in some cases, contain impurities and by-products in addition to the target monohexyl glyceryl ether or monocyclohexyl glyceryl ether, regardless of which production method is used. Examples of such impurities and by-products include residual raw materials such as hexanol and glycerin, polymers such as polyglyceryl ethers and trace components that are sources of unpleasant odors. Of these impurities and by-products, trace components that are sources of unpleasant odors are most difficult to remove. When a glyceryl ether-containing composition is blended in a cosmetic, even if the composition has an unpleasant odor, the composition can be used with no problems by masking the odor with a fragrance or the like, but the number of fragrance-free cosmetics has increased in recent years, and there is a need to remove trace components that are sources of unpleasant odors in glyceryl ethers.

In the present invention, the monohexyl glyceryl ether and monocyclohexyl glyceryl ether obtained using a method such as that described above, before undergoing the deodorization step and/or antioxidant addition step in the present invention are referred to as a monohexyl glyceryl ether-containing product and a monocyclohexyl glyceryl ether-containing product, respectively. As mentioned above, the monohexyl glyceryl ether-containing product and monocyclohexyl glyceryl ether-containing product contain impurities and by-products, but because these impurities and by-products are present in extremely small quantities, the mass of the monohexyl glyceryl ether-containing product and monocyclohexyl glyceryl ether-containing product barely changes as a result of the deodorization step, and the mass of a glyceryl ether-containing product is regarded as being the same before and after the deodorization step.

Moreover, a monohexyl glyceryl ether-containing product, a monocyclohexyl glyceryl ether-containing product or a mixture of these can be used as the glyceryl ether-containing product in the present invention, but from the perspectives of quality stability over a long period of time and antimicrobial properties, it is preferable to use a monohexyl glyceryl ether-containing product or a mixture of a monohexyl glyceryl ether-containing product and a monocyclohexyl glyceryl ether-containing product, and particularly preferable to use a monohexyl glyceryl ether-containing product. If a mixture of a monohexyl glyceryl ether-containing product and a monocyclohexyl glyceryl ether-containing product is used, the blending ratio of the two components is not particularly limited, but a monohexyl glyceryl ether:monocyclohexyl glyceryl ether mass ratio of 10:90 to 90:10 is preferred, and a mass ratio of 33:67 to 67:33 is more preferred.

Moreover, examples of compounds that are similar to the monohexyl glyceryl ether and monocyclohexyl glyceryl ether used in the present invention include glyceryl ethers having different numbers of carbon atoms in alkyl groups, dialkyl glyceryl ethers, trialkyl glyceryl ethers, alkyl glyceryl esters, compounds obtained by adding alkylene oxides to these compounds, and alkyl ether compounds of other polyhydric alcohols, and some of these types of compounds are known to exhibit effects as antimicrobial agents. However, other compounds such as these may not be able to exhibit sufficient antimicrobial properties when blended in cosmetics in some cases, and are poor in terms of practicability. In addition, problems such as oxidative degeneration, decomposition over time and generation of unpleasant odors during storage are not observed in many cases with these types of compound because stability is high and oxidative degeneration and decomposition over time barely occur even when the compounds are stored for long periods of time in high temperature environments and the like, and there is little need for measures to tackle these problems.

The deodorization step in the present invention is a step in which deodorization is carried out by bringing a glyceryl ether-containing product selected from the group consisting of a monohexyl glyceryl ether-containing product, a monocyclohexyl glyceryl ether-containing product and a mixture of these into contact with water vapor in a reduced pressure environment having a pressure of 0.10 kPa or more and 10 kPa or less for a period of 60 minutes or more and 600 minutes or less, thereby removing trace components that are the causes of unpleasant odors and oxidative degeneration, such as impurities and by-products. The method for bringing the glyceryl ether-containing product into contact with water vapor in a reduced pressure environment in this case is not particularly limited, but it is possible to use a method comprising, for example, introducing water vapor under conditions whereby the pressure in the reduced pressure environment is maintained within this range and then bringing the glyceryl ether-containing product into contact with the water vapor. If the pressure in the reduced pressure environment in this case is 0.10 kPa or more and 10 kPa or less, it is possible to obtain a glyceryl ether-containing composition in which quality can be maintained for a long period of time, but pressure conditions are preferably 0.50 kPa to 7.0 kPa, and more preferably 1.0 kPa or more and 5.0 kPa or less, from the perspectives of quality stability of the glyceryl ether-containing composition, productivity and yield. In addition, the temperature of the reduced pressure environment is not particularly limited, but is, for example, 60° C. or higher and 160° C. or lower, preferably 80° C. or higher and 140° C. or less, and more preferably 90° C. or higher and 130° C. or lower.

By setting the length of contact with the water vapor to be 60 minutes or more and 600 minutes or less, a glyceryl ether-containing composition in which quality can be maintained for a long period of time can be obtained with high productivity and high yield, but the length of contact is preferably 60 minutes or more and 300 minutes or less, and more preferably 60 minutes or more and 180 minutes or less, from the perspectives of quality stability of the glyceryl ether-containing composition and productivity.

In addition, the amount of water vapor introduced when introducing water vapor under conditions whereby the pressure in the reduced pressure atmosphere is maintained within this range is not particularly limited, but from the perspectives of quality stability of the glyceryl ether-containing composition, productivity and yield, it is preferable to introduce and contact 0.1 to 50 parts by mass, more preferably 0.5 to 30 parts by mass, and further preferably 1 to 10 parts by mass, per hour relative to 100 parts by mass of the glyceryl ether-containing product. In addition, from the perspectives of quality stability of the obtained glyceryl ether-containing composition, productivity and yield, it is preferable to bring 100 parts by mass of the glyceryl ether-containing product into contact with 1 to 50 parts by mass of water vapor, more preferably 3 to 20 parts by mass of water vapor, and further preferably 5 to 15 parts by mass of water vapor, in the reduced pressure environment throughout the entire deodorization step of the present invention as a whole. Moreover, when introducing and contacting the water vapor, gases other than water vapor, such as nitrogen, may be introduced at the same time as long as the advantageous effect of the present invention is not impaired.

An explanation will now be given of the addition step in which an antioxidant containing d-α-tocopherol is added to the glyceryl ether at a quantity of 0.05 to 0.30 parts by mass relative to 100 parts by mass of the glyceryl ether-containing product. The present invention is characterized by adding an antioxidant containing d-α-tocopherol as an antioxidant. In cases where only an antioxidant that is similar to d-α-tocopherol is added as an antioxidant, such as cases where only dl-α-tocopherol (a synthetic tocopherol) or d-α-tocopherol acetate is added, problems occur in terms of practicability due to long term quality stability being poor. Moreover, antioxidants other than d-α-tocopherol (for example, dl-α-tocopherol, d-α-tocopherol acetate and other well-known antioxidants) may additionally be used in the present invention, but from the perspective of long term quality stability, it is preferable for 50 mass % or more and 100 mass % or less of the entire amount of antioxidant in the glyceryl ether-containing composition to be d-α-tocopherol, more preferably 75 mass % or more and 100 mass % or less, and particularly preferable 100 mass % (that is, it is particularly preferable for the antioxidant to consist of d-α-tocopherol).

If the added quantity of the antioxidant is 0.05 to 0.30 parts by mass relative to 100 parts by mass of the glyceryl ether-containing product, it is possible to obtain a glyceryl ether-containing composition that exhibits excellent long term quality stability and antimicrobial properties. In addition, in cases where the glyceryl ether-containing product is a monohexyl glyceryl ether-containing product, the added quantity of the antioxidant is more preferably 0.10 to 0.30 parts by mass, and further preferably 0.15 to 0.25 parts by mass, relative to 100 parts by mass of the monohexyl glyceryl ether-containing product from the perspectives of long term quality stability and antimicrobial properties. In addition, in cases where the glyceryl ether-containing product is a monocyclohexyl glyceryl ether-containing product, the added quantity of the antioxidant is more preferably 0.05 to 0.20 parts by mass, and further preferably 0.07 to 0.15 parts by mass, relative to 100 parts by mass of the monocyclohexyl glyceryl ether-containing product from the perspectives of long term quality stability and antimicrobial properties.

The method for producing the glyceryl ether-containing composition of the present invention is a method that includes the deodorization step and addition step mentioned above as essential steps, and it is possible to carry out the addition step after the deodorization step or carry out the deodorization step after the addition step, but it is preferable to carry out the addition step after the deodorization step from the perspective of achieving the advantageous effects of the present invention. In addition, the method for producing the glyceryl ether-containing composition of the present invention may include steps other than the deodorization step and addition step mentioned above as long as the advantageous effects of the present invention are not impaired.

The glyceryl ether-containing composition of the present invention is a glyceryl ether-containing composition that contains a glyceryl ether, which is selected from the group consisting of monohexyl glyceryl, monocyclohexyl glyceryl and a mixture of these and for which the total area, as measured using a solid phase microextraction GC/FID method under temperature conditions of 50° C. for 15 minutes, is 0 or more but less than 80,000 per 1 g of glyceryl ether, and an antioxidant containing d-α-tocopherol, wherein the content of the antioxidant is 0.05 to 0.30 parts by mass relative to 100 parts by mass of glyceryl ether. Here, the total area, as measured using a solid phase microextraction GC/FID method, is a value measured/calculated using the method described below.

If the glyceryl ether-containing composition of the present invention contains a glyceryl ether for which the total area, as measured using a solid phase microextraction GC/FID method, is 0 or more but less than 80,000 per 1 g of glyceryl ether, it is possible to prevent oxidative degradation, decomposition over time and generation of unpleasant odors during storage and maintain quality over a long period of time. From the perspectives of long term quality stability and antimicrobial properties, the glyceryl ether-containing composition of the present invention preferably contains monohexyl glyceryl ether or a mixture of monohexyl glyceryl ether and monocyclohexyl glyceryl ether, and particularly preferably contains only monohexyl glyceryl ether.

From the perspectives of long term quality stability and antimicrobial properties, the total area, as measured using a solid phase microextraction GC/FID method, of the glyceryl ether is preferably 0 or more but less than 70,000, more preferably 0 or more but less than 60,000, further preferably 0 or more and 60,000 or less, and particularly preferably 0 or more and 50,000 or less, per 1 g of glyceryl ether.

The method for setting the total area, as measured using a solid phase microextraction GC/FID method, of the glyceryl ether to fall within this range is not particularly limited, but it is possible to use, for example, a method comprising bringing the glyceryl ether into contact with water vapor in a reduced pressure environment and, more specifically, it is possible to use a method such as that described above.

The glyceryl ether-containing composition of the present invention contains 0.05 to 0.30 parts by mass of an antioxidant containing d-α-tocopherol relative to 100 parts by mass of the glyceryl ether. Antioxidants other than d-α-tocopherol (for example, dl-α-tocopherol, d-α-tocopherol acetate and other well-known antioxidants) may additionally be used as long as the advantageous effects of the present invention are not impaired, but from the perspective of long term quality stability, it is preferable for 50 mass % or more and 100 mass % or less of the entire amount of antioxidant in the glyceryl ether-containing composition to be d-α-tocopherol, more preferably 75 mass % or more and 100 mass % or less, and particularly preferably 100 mass % (that is, it is particularly preferable for the antioxidant to consist of d-α-tocopherol).

For example, in cases where the glyceryl ether consists of monohexyl glyceryl, the content of the antioxidant is more preferably 0.10 to 0.30 parts by mass, and further preferably 0.15 to 0.25 parts by mass, relative to 100 parts by mass of the monohexyl glyceryl ether from the perspectives of long term quality stability and antimicrobial properties. In addition, in cases where the glyceryl ether consists of monocyclohexyl glyceryl ether, the content of the antioxidant is more preferably 0.05 to 0.20 parts by mass, and further preferably 0.05 to 0.15 parts by mass, relative to 100 parts by mass of the monocyclohexyl glyceryl ether from the perspectives of long term quality stability and antimicrobial properties.

The glyceryl ether-containing composition of the present invention preferably has a Hazen color number (APHA) of 10 to 50 from the perspectives of color at the time of use and control at the time of production and the time of storage. This Hazen color number (APHA) is a value measured in accordance with the APHA (American Public Health Association) method in the Japan Oil Chemists' Society's standard methods for the analysis of fats and oils II.C.1.5., and is obtained by quantifying the color of an object being measured. The present invention is advantageous because it is possible to assess whether a glyceryl ether-containing composition that contains the specified glyceryl ether and the specified antioxidant exhibits excellent long term quality stability and antimicrobial properties on the basis of the color of the composition. If the Hazen color number is less than 10, it can be difficult to assess whether a composition exhibits excellent long term quality stability and antimicrobial properties on the basis of the color of the composition, and if the Hazen color number exceeds 50, the color of the composition at the time of use may be undesirable and antimicrobial properties may deteriorate. In addition, from the perspective of achieving the advantageous effects of the present invention, a glyceryl ether-containing composition having a Hazen color number of 10 to 30 is more preferred, and a glyceryl ether-containing composition having a Hazen color number of 10 to 20 is even further preferred.

The glyceryl ether-containing composition of the present invention may contain other components such as solvents if necessary, but from perspectives such as long term stability and transportation convenience, it is preferable for the glyceryl ether-containing composition to consist of only a glyceryl ether and an antioxidant that satisfy the conditions mentioned above.

The glyceryl ether-containing composition of the present invention can be used in, for example, a cosmetic or a detergent by being blended or added as an antimicrobial agent.

The cosmetic composition of the present invention contains 0.10 to 10 parts by mass of the glyceryl ether-containing composition mentioned above. The blending quantity of the glyceryl ether-containing composition of the present invention in the cosmetic composition is preferably 0.20 mass % to 5.0 mass %, more preferably 0.30 mass % to 3.0 mass %, and even further preferable 0.50 mass % to 2.0 mass %, relative to the overall amount of the cosmetic composition. If this blending quantity exceeds 10 mass %, advantageous effects commensurate with the higher blending quantity may not be achieved and problems such as precipitation and separation may occur, and if this blending quantity is less than 0.10 mass %, advantageous effects as an antimicrobial agent may not be achieved.

Specific applications of the cosmetic composition of the present invention are not particularly limited, and include toiletry products such as shampoos and conditioners, and examples of these applications include skin lotions, cosmetic liquids, milky lotions, creams, face washing foams, cleansing milks, cleansing lotions, hair tonics, hair liquids, setting lotions, hair bleaches, color rinses, permanent wave liquids, lipsticks, packs, foundations, eaux de cologne, shampoos, conditioners, treatments, sunscreens, deodorants, perfumes, cleansing oils and cosmetic oils. In all of these applications, the cosmetic composition of the present invention can prevent oxidative degeneration, decomposition over time and generation of unpleasant odors in the glyceryl ether-containing composition and can maintain the quality of the cosmetic composition over a long period of time.

Some of the cosmetic compositions listed above are constituted mainly from water, such as skin lotions, some are constituted mainly from oil-soluble components, such as cosmetic oils, and some are constituted from both water and oil-soluble components, such as milky lotions and creams. The present invention achieves advantageous effects as a cosmetic composition constituted mainly from water and as a cosmetic composition constituted mainly from oil-soluble components, but in order to achieve the advantageous effects of the present invention more effectively, a cosmetic composition containing both water and oil-soluble components is preferred. Furthermore, the antimicrobial agent of the present invention achieves better antimicrobial properties and long term stability compared with other microbial agents in cosmetic compositions containing 0.5 mass % or more of water and 0.5 mass % or more of oil-soluble components, the antimicrobial agent of the present invention achieves even better antimicrobial properties compared with other microbial agents in cosmetic compositions containing 1 mass % or more of water and 1 mass % or more of oil-soluble components, the antimicrobial agent of the present invention achieves even better antimicrobial properties compared with other microbial agents in cosmetic compositions containing 5 mass % or more of water and 5 mass % or more of oil-soluble components, the antimicrobial agent of the present invention achieves the best antimicrobial properties compared with other microbial agents in cosmetic compositions in the form of W/O and O/W emulsions. Moreover, upper limits for the concentration of water and the concentration of oil-soluble components in the cosmetic composition of the present invention are generally 99 mass %, and preferably 95 mass %.

Oil-soluble components as mentioned here means components having a solubility in water of less than 1 g/100 ml. In cosmetic compositions containing components having low solubility in water, the advantageous effects of the glyceryl ether-containing composition of the present invention as an antimicrobial agent are particularly prominent. Examples of preferred components among such oil-soluble components include higher alcohols having 8 or more carbon atoms, fatty acids having 10 or more carbon atoms, fatty acid esters having 8 or more carbon atoms, hydrocarbons having 10 or more carbon atoms, natural oils and fats, synthetic oils and fats, natural waxes, silicone compounds having a kinematic viscosity of 1 $mm^2/s$ or more, polyalkylene glycol-based compounds which consist of one or two or more oxyalkylene groups having 3 or more carbon atoms and which have a weight average molecular weight of 1000 or more, and non-ionic surfactants having HLB values of 10 or less.

Examples of higher alcohols having 8 or more carbon atoms include octyl alcohol, decyl alcohol, lauryl alcohol, myristyl alcohol, cetyl alcohol, isocetyl alcohol, stearyl alcohol, isostearyl alcohol, oleyl alcohol, hexadecyl alcohol, octyldodecanol, decyltetradecanol, tetradecyloctadecanol, dodecylhexadecanol, hexyldecanol and behenyl alcohol.

Examples of fatty acids having 10 or more carbon atoms include capric acid, lauric acid, myristic acid, palmitic acid, stearic acid, isostearic acid, oleic acid, hydroxystearic acid, behenic acid and undecylenic acid.

Examples of fatty acid esters having 8 or more carbon atoms include cetyl caprate, hexyl laurate, myristyl myristate, isostearyl palmitate, isopropyl isostearate, decyl oleate, isopropyl myristate, cetyl octanoate, cetyl ethylhexanoate, octyl isononanoate, hexyldecyl dimethyloctanoate, diethyl phthalate, diethyl isophthalate, diisostearyl adipate, diisopropyl sebacate, glycol distearate, neopentyl glycol diethylhexanoate and octyl oxystearate.

Examples of hydrocarbons having 10 or more carbon atoms include isododecane, isohexadecane, liquid paraffin, Vaseline, squalane, squalene, microcrystalline waxes, mineral oils, hydrogenated polyisobutene, hydrogenated polydecene and polydecene.

Examples of natural oils and fats include almond oil, avocado oil, Shea butter, sunflower seed oil, macadamia nut oil, lanolin, reduced lanolin, mink oil, cocoa butter, coconut oil, palm oil, palm kernel oil, hydrogenated coconut oil, hydrogenated palm oil, hydrogenated palm kernel oil, camellia oil, sesame oil, castor oil, olive oil, soybean oil and beef tallow.

Examples of synthetic oils and fats include glyceryl tricaprate, glyceryl tricaprylate, glyceryl trioctanoate, glyceryl triisostearate, glyceryl tribehenate, glyceryl trihydroxystearate, and transesterification oils and fats in which the fatty acid composition is altered through transesterification of these synthetic oils and fats and natural oils and fats.

Examples of natural waxes include carnauba wax, candelilla wax, rice bran wax and beeswax.

Examples of silicone compounds having a kinematic viscosity of 1 mm$^2$/s or more include silicones (dimethylpolysiloxane), alkyl-modified silicones and polyether-modified silicones.

Examples of polyalkylene glycol-based compounds which consist of one or two or more oxyalkylene groups having 3 or more carbon atoms and which have a weight average molecular weight of 1000 or more include polypropylene glycol, polybutylene glycol, polystyrene glycol, polypropylene glycol alkyl ethers, polypropylene glycol alkyl esters, and block and random copolymers of polypropylene glycol and polybutylene glycol.

Examples of non-ionic surfactants having HLB values of 10 or less include glycerol monostearate, ethylene glycol monostearate, sorbitan monooleate, sorbitan monostearate, ethylene glycol monolauryl ether, diethylene glycol monooleyl ether and block copolymers and random copolymers of polyethylene glycol and polypropylene glycol. Moreover, a non-ionic surfactant having an HLB value of 5 or less is preferred.

Components able to be blended in cosmetic compositions (excluding the oil-soluble components mentioned above), such as surfactants, thickening agents, powders (pigments, dyes and resins), other antimicrobial agents, fragrances, humectants, physiologically active components, salts, solvents, antioxidants, chelating agents, pearlescent agents, neutralizing agents, pH-adjusting agent and enzymes can be further blended, as appropriate, in the cosmetic composition of the present invention according to the constitution and intended use of the cosmetic composition.

Examples of surfactants include anionic surfactants, non-ionic surfactants having HLB values of more than 10, cationic surfactants and amphoteric surfactants, and examples of anionic surfactants include higher fatty acid salts, higher alcohol sulfonic acid ester salts, sulfurized olefin salts, higher alkylsulfonic acid salts, α-olefin sulfonic acid salts, sulfated fatty acid salts, sulfonated fatty acid salts, phosphoric acid ester salts, sulfuric acid ester salts of fatty acid esters, glyceride sulfuric acid ester salts, sulfonic acid salts of fatty acid esters, methyl α-sulfofatty acid ester salts, polyoxyalkylene alkyl ether sulfuric acid ester salts, polyoxyalkylene alkyl phenyl ether sulfuric acid ester salts, polyoxyalkylene alkyl ether carboxylic acid salts, acylated peptides, sulfuric acid ester salts of fatty acid alkanolamides or alkylene oxide adducts thereof, sulfosuccinic acid esters, alkylbenzene sulfonic acid salts, alkylnaphthalene sulfonic acid salts, alkylbenzimidazole sulfonic acid salts, polyoxyalkylene sulfosuccinic acid salts, N-acyl-N-methyltaurine salts, N-acylglutamic acids and salts thereof, acyloxyethane sulfonic acid salts, alkoxyethane sulfonic acid salts, N-acyl-β-alanine and salts thereof, N-acyl-N-carboxyethyltaurine and salts thereof, N-acyl-N-carboxymethylglycine and salts thereof, acyl lactic acid salts, N-acylsarcosine salts, alkyl- or alkenyl-aminocarboxymethyl sulfuric acid salts, and mixtures of one or more of these types.

Examples of non-ionic surfactants having HLB values of 10 include polyoxyethylene alkyl ethers, polyoxyethylene alkenyl ethers, polyoxyethylene-polyoxypropylene alkyl ethers (in which the manner in which ethylene oxide and propylene are added can be random or as blocks), polyethylene glycol-propylene oxide adducts and polypropylene glycol-ethylene oxide adducts.

Examples of cationic surfactants include alkyl (or alkenyl) trimethyl ammonium salts, dialkyl (or dialkenyl) dimethyl ammonium salts, alkyl (or alkenyl) quaternary ammonium salts, mono- or di-alkyl (or alkenyl) quaternary ammonium salts having an ether group, an ester group or an amide group, alkyl (or alkenyl) pyridinium salts, alkyl (or alkenyl) dimethylbenzyl ammonium salts, alkyl (or alkenyl) isoquinolinium salts, dialkyl (or alkenyl) morphonium salts, polyoxyethylene alkyl (or alkenyl) amines, alkyl (or alkenyl) amine salts, polyamine fatty acid derivatives, amyl alcohol fatty acid derivatives, benzalkonium chloride and benzethonium chloride.

Examples of amphoteric surfactants include carboxybetaines, sulfobetaines, phosphobetaines, amidoamino acids and imidazolinium betaine-based surfactants.

The usage quantity of these surfactants varies according to the type of cosmetic composition to which a surfactant is to be added, but is preferably 0.1 mass % to 30 mass %, and more preferably 0.5 mass % to 20 mass %, relative to total amount of the cosmetic composition.

Examples of thickening agents include dimethyldiallylammonium chloride.acrylamide copolymers, acrylamide/acrylic acid/dimethyldiallylammonium chloride copolymers, cellulose and derivatives thereof, keratin and collagen and derivatives thereof, calcium alginate, pullulan, agar, gelatin, tamarind seed polysaccharides, xanthan gum, carrageenan, high methoxyl pectin, low methoxyl pectin, guar gum, gum Arabic, crystalline cellulose, arabinogalactan, karaya gum, tragacanth gum, alginic acid, albumin, casein, curdlan, β-glucan, gellan gum and dextran. The usage quantity of these thickening agents varies according to the type of cosmetic composition to which a thickening agent is to be added, but is preferably 0.01 mass % to 10 mass %, and more preferably 0.1 mass % to 8 mass %, relative to the total amount of the cosmetic composition.

Examples of powders include dyes such as Red No. 201, Yellow No. 4, Blue No. 1 and Black No. 401, lake dyes such as Yellow No. 4 Al lake and Yellow No. 203 Ba lake, polymers such as nylon powders, silk powders, silicone powders, cellulose powders, spherical silicone elastomer powders and polyethylene powders, coloring pigments such as yellow iron oxide, red iron oxide, chromium oxide, carbon black, ultramarine blue and Prussian blue, white pigments such as zinc oxide and titanium oxide, body pigments such as talc, mica, sericite and kaolin, pearlescent pigments such as mica and titanium, metal salts such as barium sulfate, calcium carbonate, magnesium carbonate and magnesium silicate, inorganic powders such as silica and alumina, bentonite, smectite and boron nitride. The shape of these powders is not particularly limited (spherical, rod-like, needle-like, lamellar, amorphous, flaky, spindle-like, or the like). The usage quantity of these powders varies according to the type of cosmetic composition to which a powder is to be added, but is preferably 0.01 mass % to 10 mass %, and more preferably 0.1 mass % to 5 mass %, relative to the total amount of the cosmetic composition.

Examples of humectants include diethylene glycol monoethyl ether, biopolymers such as deoxyribonucleic acid, mucopolysaccharides, sodium hyaluronate, sodium chondroitin sulfate, collagen, elastin, chitin, chitosan and hydrolyzed eggshell membrane, amino acids, sodium lactate, urea, sodium pyrrolidone carboxylate, betaines and whey. The usage quantity of these humectants varies according to the type of cosmetic composition to which a humectant is to be added, but is preferably 0.1 mass % to 30 mass %, and more preferably 0.5 mass % to 20 mass %, relative to the total amount of the cosmetic composition.

Examples of solvents include purified water, ethanol, propanol and isopropanol.

The method for improving the quality stability of the glyceryl ether of the present invention comprises adding d-α-tocopherol to a deodorized glyceryl ether selected from the group consisting of deodorized hexyl glyceryl ether, cyclohexyl glyceryl ether and a mixture of these so as to attain a Hazen color number (APHA) of 10 to 50. By adjusting the added quantity through color, it is possible to conveniently prepare a glyceryl ether having excellent long term quality stability. In addition, because the color changes following the addition, it is easy to assess whether or not addition has taken place and this is excellent as a method for improving quality stability.

EXAMPLES

The present invention will now be explained in detail through the use of examples. Moreover, in the examples etc. given below, % means mass % unless explicitly indicated otherwise.

Production of Glyceryl Ether

The monohexyl glyceryl ether and monocyclohexyl glyceryl ether used in the present invention were produced using the methods described below.

Synthesis Example 1

2.7 g of a monohexyl glyceryl ether-containing product was obtained by reacting 3.0 g of hexanol and 2.1 g of epichlorohydrin at 80° C. for 4 hours so as to obtain hexyl glycidyl ether as an intermediate, and then hydrolyzing the obtained hexyl glycidyl ether.

Synthesis Example 2

2.7 g of a monocyclohexyl glyceryl ether-containing product was obtained by reacting 3.2 g of cyclohexanol and 2.1 g of epichlorohydrin at 80° C. for 4 hours so as to obtain cyclohexyl glycidyl ether as an intermediate, and then hydrolyzing the obtained cyclohexyl glycidyl ether.

Deodorization Step 2.7 g of each of the monohexyl glyceryl ether-containing product and monocyclohexyl glyceryl ether-containing product produced in Synthesis Example 1 and Synthesis Example 2 were placed in flasks, and deodorization was carried out for the periods of time shown in Table 1 and Table 2 by introducing water vapor into each flask at a flow rate of 3 parts by mass/h relative to 100 parts by mass of the glyceryl ether-containing product while evacuating the flasks with a vacuum pump, thereby bringing the glyceryl ether-containing product into contact with the water vapor in an environment having a temperature of 110° C. and a pressure of 4 kPa. Moreover, a treatment time of 0 minutes means that deodorization was not carried out.

Measurement of Total Area

The total area, as measured using a solid phase microextraction GC/FID method, was measured for each of glyceryl ethers 1 to 12 following the deodorization. Specifically, 1.0 g of a deodorized glyceryl ether was placed in a container, impurities and by-products contained in the glyceryl ether were adsorbed on fibers of DVB/PDMS (divinylbenzene dispersed/polydimethylsiloxane) by heating for 15 minutes at 50° C., these fibers were placed in a holder, and measurements were carried out using gas chromatography (apparatus: GC-2014, produced by Shimadzu Corporation) under the measurement conditions shown below. The total area attributable to components other than the glyceryl ethers was then calculated on the basis of a JIS K 0114 (2012) absolute calibration curve using the analysis software of the chromatography apparatus. Calculation results are shown in Table 1 and Table 2.

Measurement Conditions

Column: InertCap (registered trademark) PureWAX (length 30 m, film pressure 0.50 μm, inner diameter 0.25 μm)
Carrier gas: Helium
Carrier flow rate: 124.5 mL/min
Injection port temperature: 260° C.
Detector temperature: 260° C.

TABLE 1

|  | Glyceryl ether 1 | Glyceryl ether 2 | Glyceryl ether 3 | Glyceryl ether 4 | Glyceryl ether 5 | Glyceryl ether 6 | Glyceryl ether 7 |
| --- | --- | --- | --- | --- | --- | --- | --- |
| Raw material | Monohexyl glyceryl ether produced in Synthesis Example 1 | | | | | | |
| Deodorization time | 0 minutes | 15 minutes | 30 minutes | 45 minutes | 60 minutes | 120 minutes | 180 minutes |
| Total area | 200,000 | 120,000 | 80,000 | 80,000 | 60,000 | 50,000 | 50,000 |

TABLE 2

|  | Glyceryl ether 8 | Glyceryl ether 9 | Glyceryl ether 10 | Glyceryl ether 11 | Glyceryl ether 12 |
|---|---|---|---|---|---|
| Raw material | Monocyclohexyl glyceryl ether produced in Synthesis Example 2 | | | | |
| Deodorization time | 0 minutes | 30 minutes | 45 minutes | 60 minutes | 180 minutes |
| Total area | 300,000 | 150,000 | 90,000 | 50,000 | 50,000 |

Addition Step

Glyceryl ether-containing compositions were produced by adding antioxidants to deodorized glyceryl ethers under conditions shown in Table 3 or Table 4. The Hazen color numbers (APHA) of the produced glyceryl ether-containing compositions were measured in accordance with the APHA (American Public Health Association) method in the Japan Oil Chemists' Society's standard methods for the analysis of fats and oils II.C.1.5., and the measurement results are shown in Table 3 and Table 4.

Antioxidants Used
(Antioxidant 1) d-α-tocopherol (product name: Tocopherol 100, produced by The Nisshin OilliO Group, Ltd.)
(Antioxidant 2) dl-α-tocopherol (product name: E Oil 1000, produced by Riken Vitamin Co., Ltd.)
(Antioxidant 3) d-α-tocopherol acetate (special grade reagent G, produced by Tokyo Chemical Industry Co., Ltd.)

Deodorizing Properties Test

The deodorizing properties of the produced glyceryl ether-containing compositions were measured immediately after production and after being stored in the dark for 2 months and 4 months at temperatures of 25° C./40° C./60° C. As a method for evaluating deodorizing properties, seven testers gave evaluation scores of 1 to 10 points, with a score of 10 points being given in a case where samples stored at any temperature had no odor whatsoever and a score of 1 point being given in a case where a sample stored at any temperature had a strong odor, the total scores of the testers were calculated, with a total score of 60 points or more being evaluated as +++, a score of 45 points or more but less than 60 points being evaluated as ++, and a score of less than 45 points being evaluated as +. The evaluation results are shown in Tables 3 and 4.

Stability Test

The structural stability of the produced glyceryl ether-containing compositions was measured immediately after production and after being stored in the dark for 2 months and 4 months at temperatures of 25° C./40° C./60° C. As a method for evaluating structural stability, each glyceryl ether-containing composition was measured by means of a GC/FID method using a gas chromatograph (apparatus name: GC-2014, produced by Shimadzu Corporation), and the ratio of the peak area attributable to each glyceryl ether was calculated by means of an area percentage method using the analysis software of the chromatography apparatus and taken to be the purity, and a case where the purity of the sample having the lowest sample following storage at 25° C./40° C./60° C. was 99.5% or higher was evaluated as +++, a purity of 99.0% or higher but less than 99.5% was evaluated as ++, and a purity of less than 99.0% was evaluated as +. The evaluation results are shown in Tables 3 and 4.

TABLE 3

|  |  |  | Example 1 | Example 2 | Comparative Example 1 | Comparative Example 2 | Comparative Example 3 |
|---|---|---|---|---|---|---|---|
| Glyceryl ether-containing composition | Glyceryl ether | | Glyceryl ether 7 100 parts by mass | Glyceryl ether 7 100 parts by mass | Glyceryl ether 7 100 parts by mass | Glyceryl ether 7 100 parts by mass | Glyceryl ether 7 100 parts by mass |
|  | Antioxidant | | Antioxidant 1 0.10 parts by mass | Antioxidant 1 0.20 parts by mass | Antioxidant 2 0.20 parts by mass | Antioxidant 3 0.20 parts by mass | None |
| Evaluation results | Hazen color number | | 10 | 20 | 20 | 30 | <10 |
|  | Deodorizing properties | Immediately after production | +++ | +++ | +++ | +++ | +++ |
|  |  | After 2 months | ++ | +++ | +++ | + | + |
|  |  | After 4 months | ++ | +++ | ++ | + | + |
|  | Stability | Immediately after production | +++ | +++ | +++ | +++ | +++ |
|  |  | After 2 months | ++ | +++ | + | + | + |
|  |  | After 4 months | ++ | +++ | + | + | + |

TABLE 4

|  |  |  | Example 3 | Example 4 | Comparative Example 4 | Comparative Example 5 | Comparative Example 6 |
|---|---|---|---|---|---|---|---|
| Glyceryl ether-containing composition | Glyceryl ether | | Glyceryl ether 12 100 parts by mass | Glyceryl ether 12 100 parts by mass | Glyceryl ether 12 100 parts by mass | Glyceryl ether 12 100 parts by mass | Glyceryl ether 12 100 parts by mass |
|  | Antioxidant | | Antioxidant 1 0.05 parts by mass | Antioxidant 1 0.10 parts by mass | Antioxidant 2 0.10 parts by mass | Antioxidant 3 0.10 parts by mass | None |

TABLE 4-continued

|  |  | | Example 3 | Example 4 | Comparative Example 4 | Comparative Example 5 | Comparative Example 6 |
|---|---|---|---|---|---|---|---|
| Evaluation results | Hazen color number | | 10 | 10 | 10 | 30 | <10 |
| | Deodorizing properties | Immediately after production | +++ | +++ | +++ | +++ | +++ |
| | | After 2 months | ++ | +++ | +++ | + | + |
| | | After 4 months | ++ | +++ | ++ | + | + |
| | Stability | Immediately after production | +++ | +++ | +++ | +++ | +++ |
| | | After 2 months | ++ | +++ | + | + | + |
| | | After 4 months | ++ | +++ | + | + | + |

From the results above, it is understood that according to the present invention, it is possible to obtain a glyceryl ether-containing composition in which oxidative degradation, decomposition over time and generation of unpleasant odors during storage can be adequately prevented and quality can be maintained over a long period of time.

The invention claimed is:

1. A method for producing a glyceryl ether-containing composition, the method comprising:

a deodorization step of bringing a glyceryl ether-containing product selected from the group consisting of a monohexyl glyceryl ether-containing product, a monocyclohexyl glyceryl ether-containing product and a mixture thereof into contact with water vapor in an environment having a reduced pressure of 0.10 kPa or more and 10 kPa or less for 60 minutes or more and 600 minutes or less; and an addition step of adding 0.05 to 0.30 parts by mass of an antioxidant consisting of d-α-tocopherol to 100 parts by mass of the glyceryl ether-containing product, wherein the monohexyl glyceryl ether-containing product is produced by a method comprising reacting hexanol with epichlorohydrin and then hydrolyzing an obtained hexyl glycidyl ether and, wherein the monocyclohexyl glyceryl ether-containing product is produced by a method comprising reacting cyclohexanol with epichlorohydrin and then hydrolyzing an obtained cyclohexyl glycidyl ether.

2. The method for producing a glyceryl ether-containing composition according to claim 1, wherein the glyceryl ether-containing product is selected from the group consisting of a monohexyl glyceryl ether-containing product and a mixture of a monohexyl glyceryl ether-containing product and a monocyclohexyl glyceryl ether-containing product.

* * * * *